United States Patent [19]

Ozawa et al.

[11] Patent Number: 4,608,994
[45] Date of Patent: Sep. 2, 1986

[54] PHYSIOLOGICAL MONITORING SYSTEM

[75] Inventors: Lyuji Ozawa, Glencoe; Hans Schmidt, Wood Dale; Mike Hsu, Franklin Park; Arye Perlmutter, Skokie, all of Ill.

[73] Assignee: Matsushita Electric Industrial Co., Ltd., Osaka, Japan

[21] Appl. No.: 683,856

[22] Filed: Dec. 20, 1984

[51] Int. Cl.$^4$ .............................................. A61B 5/00
[52] U.S. Cl. .................................................. 128/670
[58] Field of Search ............... 128/670, 680, 681, 682, 128/683, 687, 690, 710

[56] References Cited

U.S. PATENT DOCUMENTS

| | | | |
|---|---|---|---|
| 3,101,082 | 8/1963 | Steen et al. | 128/680 |
| 3,126,885 | 3/1964 | Hinman | 128/680 |
| 3,230,950 | 1/1966 | Buffington | 128/680 |
| 4,271,844 | 6/1981 | Croslin | 128/681 |
| 4,397,317 | 8/1983 | Villa-Real | 128/680 |
| 4,408,614 | 10/1983 | Weaver et al. | 128/680 |
| 4,461,266 | 7/1984 | Hood, Jr. et al. | 128/680 |
| 4,484,584 | 11/1984 | Vermura | 128/680 |

OTHER PUBLICATIONS

Hinman et al, Am. Heart J., May 1982, pp. 663–668.
Silas et al, Br. Heart J., 1980, vol. 43, pp. 202–205.
Kennedy et al, American Heart Journal, Oct. 1983, pp. 717–722.
Ramsey, III, "Medical and Biological Engineering and Computing", v. 17, No. 1, Jan. 1979, pp. 11–18.
Technical Note, "Medical and Biological Engineering and Computing", vol. 21, No. 3, pp. 229–231.

Primary Examiner—William E. Kamm

[57] ABSTRACT

A physiological monitoring device receives a plurality of physiological measurements, including the user's diastolic and systolic blood pressure, pulse rate and body temperature. The physiological measurements are stored in a memory which is controlled by a microprocessor. The microprocessor organizes the measurements and causes the measurements to be displayed for analysis on a screen in either digital or graph form, printed in either digital or graph form and/or transmitted over a phone line or other communication link for reproduction in either digital or graph from at a distant receiver located, for example, in a doctors office or hospital.

1 Claim, 7 Drawing Figures

PHYSIOLOGICAL MONITORING SYSTEM

The invention relates to the field of portable devices for storing, transmitting and printing measurements of basic physiological parameters, thereby permitting the long term monitoring of those parameters.

Over the past decade, the general public's concern with general health (nutrition, fitness etc.) has increased greatly. This rise in interest in health has been accompanied with steady increases in the cost of health care, especially hospitalization which has become prohibitive. As a result, devices which serve to eliminate the need for hospitalization or for visits to a doctor or clinic are sorely needed. Specifically, at present, if a doctor wishes to monitor on a daily basis a patients physiological state (blood pressure, pulse rate, temperature), the patient must be admitted to a hospital or make daily visits to the physician's office in order to have the measurements taken and recorded. Typically the data is collected by a professional (nurse or doctor) and recorded on data sheet which forms part of the patient's record. While this is obviously inconvenient to the patient who must either be hospitalized or make daily visits to the doctor's office (both of which invariably cause stress to the patient resulting in inflated measurements), it also requires the use of the time and skills of a professional and finally results in data which is not readily or easily reviewable by the doctor. Specifically, if the doctor wishes to review daily changes in any of the patient's physiological parameters, he must go through a lot of paper in the patient's file or take the time to arrange the data in graph form to facilitate analysis.

One alternative to the procedure outlined above is to rent to the patient the equipment necessary to monitor the desired physiological parameters, entrusting the patient to gather the measurements and record them correctly. There are several drawbacks to this alternative. One is that the patient has to be given separate devices for determining the different parameters. Another is that the patient may incorrectly record the measurements or may simply forget to record the measurements. A third disadvantage is that this could be costly to both the patient and doctor since the doctor would have to maintain an inventory of the various devices and the patient would have to rent or purchase this equipment.

An attempt to overcome the drawbacks described above is shown in U.S. Pat. No. 4,397,317 issued to Villa-Real which describes a portable blood pressure and pulse rate device for home or office use by one or more individuals. The device includes a microprocessor controlled memory for storage of these parameters as well as the user's temperature. While this device addresses some of the problems outlined above, it still does not effectively organize measurements taken over a long period of time in order to permit the doctor to quickly analyze the patient's basic physiological parameters over time. By way of illustration, in order for a doctor using the device shown in U.S. Pat. No. 4,397,317 to review, for example, the patient's pulse rate over a period of two months, he must individually recall (from the memory) the user's pulse rate for each day of the two month period. Specifically, the device can only display these pulse rate measurements in a sequential manner, one measurement after another. Thus, this system does not provide a mechanism for the quick and efficient retrieval and analysis of the information stored therein. Other drawbacks of the device of U.S. Pat. No. 4,397,317 include the inability of the patient or doctor to obtain a hard copy of the stored measurements or even of a measurement just completed and the lack of communication capabilities of the device which would permit measurements taken in a patient's home to be transmitted to other devices situated in a doctor's office or hospital. This lack of communication capability deprives the doctor of extremely current and reliable measurements which would otherwise be useful in providing immediate action, if required.

It is therefor an object of the present invention to provide a physiological monitoring device which overcomes the disadvantages of prior art devices and practices.

Another object of the present invention is to provide a physiological monitoring device which permits a user to monitor his physical condition at home, thereby assuring accurate measurements which are unaffected by the stress accompanying a visit to a doctor or hospital.

Still another object of the present invention is to provide a physiological monitoring device which collects and stores a plurality of measurements of various physiological parameters.

A further object of the present invention is to provide a physiological monitoring device which permits the transmission of measurements of various physiological parameters taken over time.

A still further object of the present invention is to provide a physiological monitoring device which provides a hard copy of measurements of various physiological parameters taken over time.

An additional object of the present invention is to provide a physiological monitoring device which organizes measurements of various physiological parameters taken over time so as to facilitate their analysis and review by a doctor.

An additional object of the present invention is to provide a physiological monitoring device which organizes in graph form measurements of various physiological parameters taken over time.

An additional object of the present invention is to provide a physiological monitoring device which permits transmission of measurements of various physiological parameters from the user's home to a doctor's office.

An additional object of the present invention is to provide a physiological monitoring device which collects and stores a plurality of measurements of various physiological parameters which is both portable and easy to use.

These and other objects are provided in accordance with the present invention, which is a physiological monitoring device which receives a plurality of physiological measurements, including the user's diastolic and systolic blood pressure, pulse rate and body temperature. The physiological measurements are stored in a memory which is controlled by a microprocessor. The microprocessor organizes the measurements and causes the measurements to be displayed for analysis on a screen in either digital or graph form, printed in either digital or graph form and/or transmitted over a phone line or other communication link for reproduction in either digital or graph form at a distant receiver located, for example, in a doctors office or hospital.

The above brief description as well as further objects, features and advantages of the present invention will be more fully understood by reference to the following detailed description of the presently preferred, but nontheless illustrative embodiments in accordance with the present invention, when taken in conjunction with the accompanying drawings, wherein:

Figure 1:
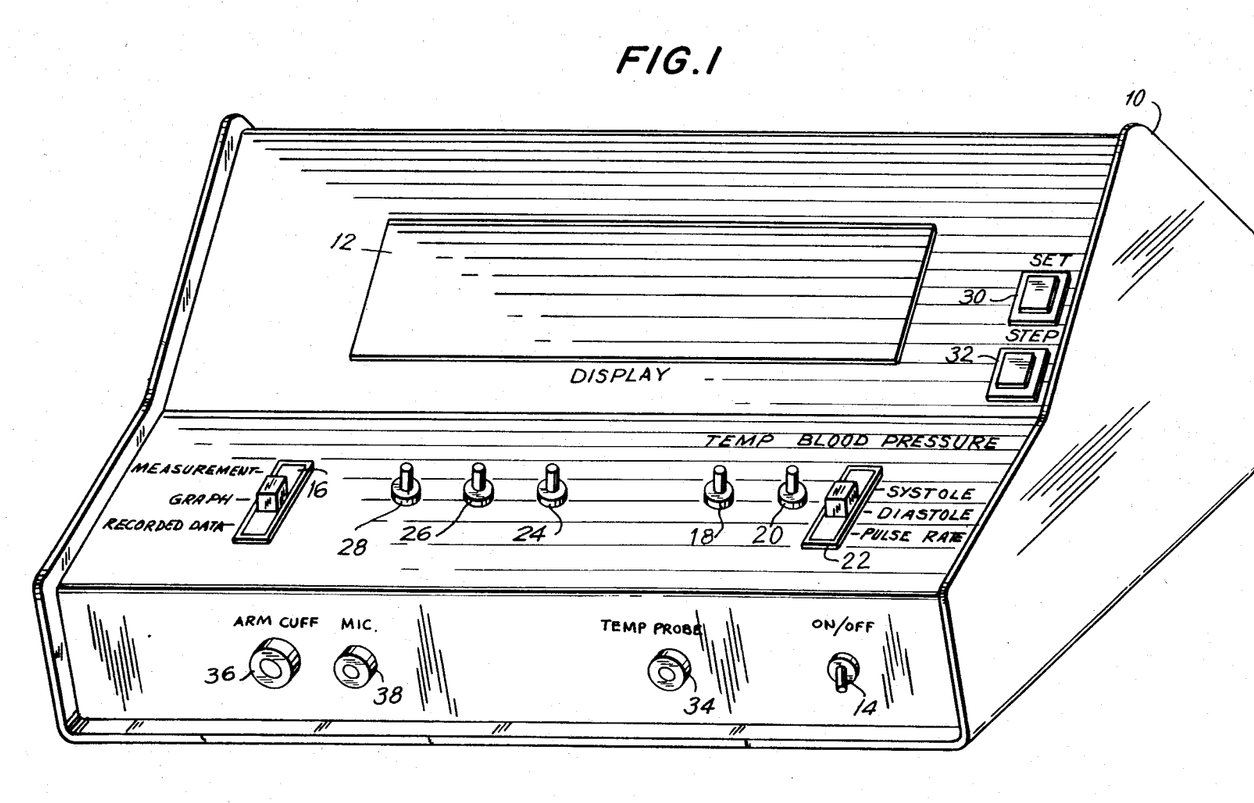
FIG. 1 is a perspective view of the housing containing the various electronic and mechanical components of the physiological monitoring device of the present invention.

Referring now to FIG. 1 the physiological monitoring device of the present invention includes a housing 10 which contains the electronic circuitry for the device and includes a standard liquid crystal display 12 capable of providing either a graphic or digital display. An on-off switch 14 serves to activate the device, which includes a three-way switch 16 having a measurement, graph and recorded data position. If the switch 16 is in the measurement position the device will examine the temperature and blood pressure switches 18 and 20 to determine which of these measurements is requested. If the switch 16 is in the graph position the device will display a graph of stored measurements taken over a given period of time (e.g. daily measurements for the past thirty days) of either the user's systolic pressure, diastolic pressure or pulse rate, depending upon the position of switch 22, i.e. in either the systole, diastole or pulse rate position. As such, switch 22 serves as a display mode switch as it determines specific values to be displayed in graph form. Finally, if switch 16 is in the recorded data position, a digital display of the stored values of the user's systolic pressure, diastolic pressure, pulse rate and temperature is provided.

Of the remaining switches on the housing 10, the memory switch 24, when activated, serves to store the most recent temperature or blood pressure measurement in a non-volatile memory. The modem switch 26, when activated causes the transmission through a telephone line of any one of the following sets of data, depending on the position of switch 16:

1. The time, date and most recent measurement will be transmitted if switch 16 is in the measurement position.
2. A graph of either the user's systolic pressure, diastolic pressure or pulse rate over a given period of time, depending upon the position of switch 22, will be transmitted if switch 16 is in the graph position.
3. All stored systolic pressure, diastolic pressure, pulse rate and temperature measurements will be transmitted if switch 16 is in the recorded data position.

Switch 28 controls a printer, not shown, which may either be part of the device 10 or a separate unit. The printer may be any of the currently available printers which are capable of interfacing with a microprocessor control circuit and printing graphs, such as standard dot matrix printers. Upon activation of switch 28, the following data will be printed depending upon the position of switch 16:

1. The time, date and most recent measurement taken will be printed if switch 16 is in the measurement position.
2. A graph of the stored measurements over a given period of time of either the user's systolic pressure, diastolic pressure or pulse rate, depending upon the position of switch 22, will be printed if switch 16 is in the graph position.
3. All stored temperature, systolic pressure, diastolic pressure and pulse rate measurements will be printed if switch 16 is in the recorded data position.

Set and step buttons 30 and 32 are located on housing 10 and used to set the date and time on an internal clock. The exact use of these buttons to set the date and time, which information is displayed in digital form on the display 12, will be described below.

Housing 10 also includes several sockets used to allow communication between the device and the apparatus used to perform the temperature and blood pressure measurements. Specifically, socket 34 is adapted to receive electronic input from a body temperature measuring device such as the thermometer shown and described in the co-pending and commonly owned U.S. patent application Ser. No. 548,679, entitled "Device for Measuring Body Temperature" and filed Nov. 4, 1983. The output from such a thermometer (in the form of electronic signals) is received by the device of the present invention through socket 34.

Socket 36 is adapted to receive one end of a hose connected to a conventional arm cuff used for taking blood pressure measurements. Preferably, housing 10 includes a convention air pump, now shown, to supply pressurized air to the arm cuff during the blood pressure measurement. Specifically, the cuff may be a pneumatic inflatable pressure cuff which is inflated and then deflated by use of the pump in order to obtain the blood pressure measurement. In addition, housing 10 includes socket 36 which communicates with a pressure measuring device which provides instantaneous values of the air pressure within the arm cuff. Co-pending and commonly owned Patent Application Ser. No. 653,938, filed Sept. 24, 1984 for "Electronic Blood Pressure and Pulse Rate Measurement Device" describes a combination pump and pressure sensor usable with a finger cuff to determine a user's blood pressure. It will be readily appreciated that such a pump and pressure sensor may be easily adapted for use in the device of the present invention, which utilized an arm cuff. Alternately, the device of the present invention could also be adapted to be used with the finger cuff shown in Application Ser. No. 653,938.

Socket 38 is adapted to receive the output of a standard Korotkoff sound detector, which detector is located within the arm cuff and used to detect the Korotkoff sounds signaling systolic and diastolic pressure. The Korotkoff or K sound detector is typically an accoustical transducer placed at an optimal location within the arm cuff.

Figure 2:
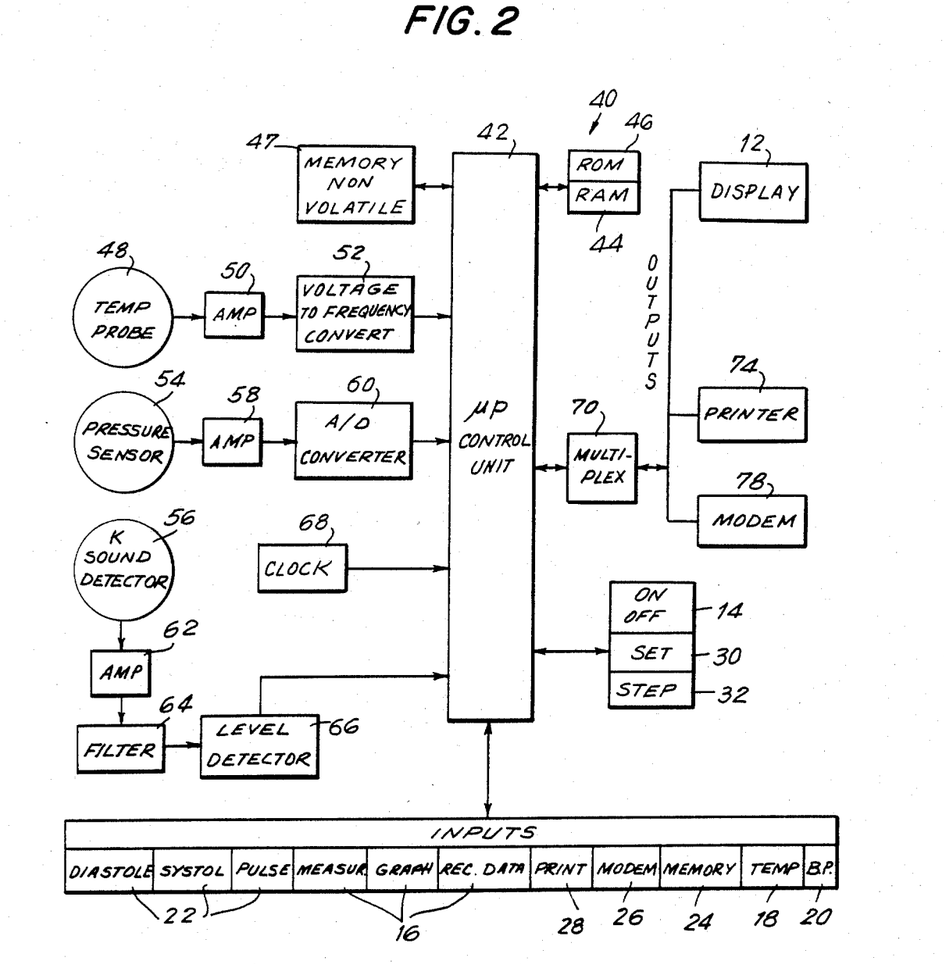
FIG. 2 is a block diagram of the electronic circuitry associated with the physiological monitoring device of the present invention.

The operation of the physiological monitor device will now be described with reference to FIGS. 2-5. Referring to FIG. 2, the electronic circuitry, indicated generally by the reference character 40, includes a microprocessor 42, a random access memory 44 used as temporary storage and a read only memory 46 in which is stored the software for the system. In addition, a non-volatile memory 48 is provided for storage of a plurality of temperature and blood pressure measurements taken over a given period of time. Use of the non-volatile memory assures that the stored data will not be lost when the device of the present invention is turned off.

The microprocessor 42 receives input regarding the body temperature of the user from a temperature probe or sensor 48. The output from the sensor is amplified by an amplifier 50 which supplies input to a voltage to frequency converter 52. The voltage to frequency converter 52 converts the amplified voltage to a pulse signal which is supplied to the microprocessor 42. The frequency of the supplied pulse signal varies with the voltage output of the amplifier 50, which in turn varies with the temperature sensed by the temperature probe 48.

The blood pressure measurements are determined through the use of a pressure sensor 54 and a Korotkoff (K) sound detector 56. Specifically, the pressure sensor 54 monitors the pressure in the arm cuff and provides input to an amplifier 58 which in turn provides input to a analog to digital converter 60. The resulting digital signals are then provided to the microprocessor 42. The Korotkoff sound detector 56 provides output in response to the Korotkoff sounds created by the accoustical turbulence of blood flow through a compressed semi-opened artery. Specifically, during the blood pressure measurement the arm cuff (typically an inflatable bladder surrounded by an unyielding cuff) is placed on the arm with the bladder carefully centered over the radial artery. The bladder is then inflated by the pump to a pressure which is 30 mm/Hg above the expected value of the systolic pressure so as to occlude the artery. The bladder is then deflated and the pressure on the occluded artery is released and a first "thud" or Korotkoff sound is detected signaling the systolic pressure measurement. The diastolic pressure is typically indicated by the disappearance of the Korotkoff sounds.

The signals generated by the K sound detector 56 in response to the Korotkoff sounds are first applied to an amplifier 62 and then to a 50–160 Hz (the frequency range for Korotkoff signals) bandpass filter 64 in order to screen out noise. A level detector (e.g. Schmidt trigger) 66 is used to further reduce noise in the relevant bandwidth. The output of the levl detector 66 is supplied to the microprocessor 42.

The date and time are maintained on a standard clock 68, the output of which may be provided to the display 12 through the microprocessor 42. The clock 68 is set through use of the step 32 and set 30 switches in a manner to be more fully described below.

The microprocessor 42 also receives input from switches 22, 16, 28, 26, 24, 18 and 20. Multiplex circuitry 70 channels the selected output to the liquid crystal display 12, or to a printer 74 or a modem 78.

Figure 3:
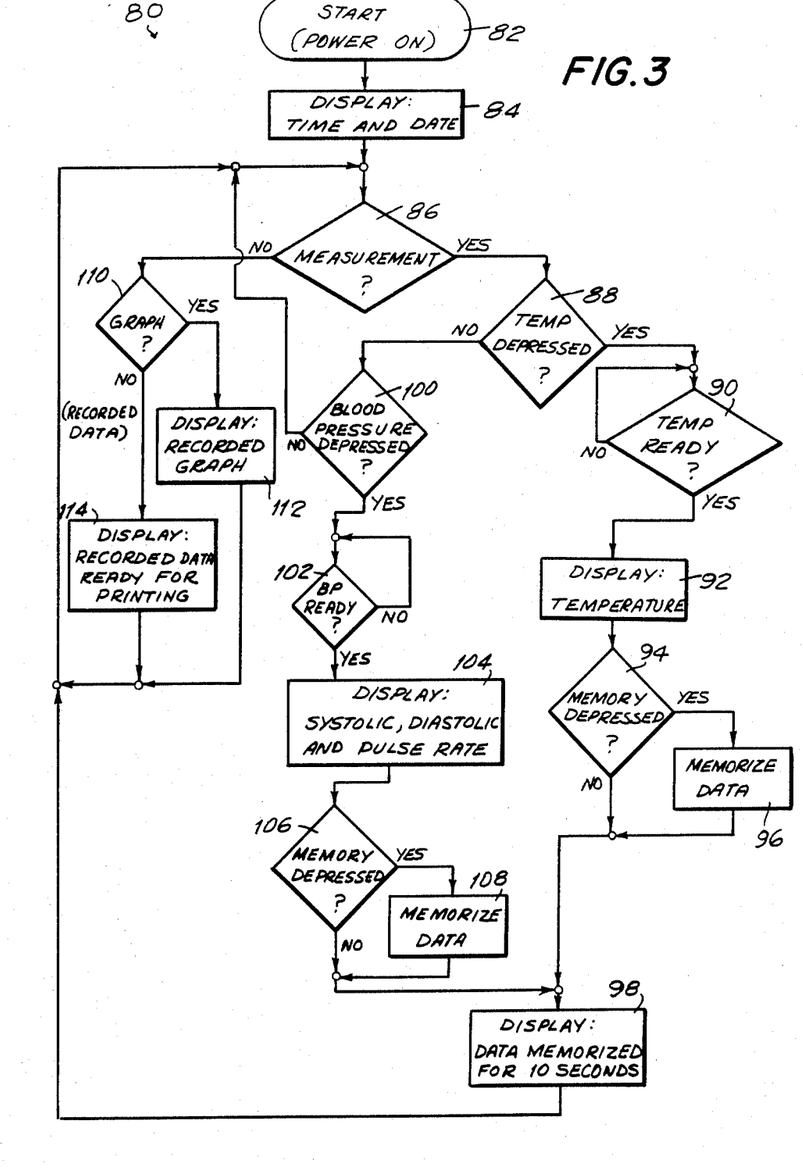
FIG. 3 is a flow chart showing the operating routine of the electronic circuitry shown in FIG. 2.

Referring now to FIG. 3, there is shown a flow chart, indicated generally by the reference numeral 80, of the operating routine or program for the physiological monitoring device of the present invention, which program permits the determination and display of the temperature, blood pressure and pulse rate of a user.

Once power is applied to the system, the time (hour, minute and second) and date (day and month) is displayed on the liquid crystal display 12 (blocks 82 and 84) and switch 16 is examined to determine the particular function requested, e.g. a temperature or blood pressure measurement (measurement), a graphic display (graph) or a listing of stored measurements (recorded data) (block 86). Specifically, if switch 16 is in the measurement position, the microprocessor 42 examines the temperature switch 18. If the temperature switch 18 is depressed, indicating the user's desire for a measurement of his body temperature, the microprocessor will await input from the temperature probe 48 (blocks 88 and 90). Once input corresponding to the body temperature is received it is displayed in digital form on the display 12 (block 92) and the memory switch 24 is examined in order to determine whether the user wishes to store this temperature measurement (blocks 92 and 94). If the memory button 24 is depressed, the temperature measurement will be stored in the non-volatile memory 48.

Preferably, the non-volatile memory 48 has sufficient storage space to store, for example, one temperature, blood pressure (systolic/diastolic ) and pulse rate measurement for each of a total of 75 days. While the microprocessor is programmed to store only one temperature, blood pressure and pulse rate measurement per day, the user is not precluded from checking his temperature, blood pressure and pulse rate several times a day. However, preferably the user stores only one set of readings per day. Alternately, the system could be set up to store two sets of measurements per day (morning and evening) and, of course, the capacity of the memory could be increased to provide more storage capability.

Regardless of whether the temperature measurement is stored in the memory 48, the display 12 will show the temperature measurement currently stored in the memory 48 for today's date for at least 10 seconds (block 98). The program then returns to block 86 and again examines switch 16.

Returning now to block 88, if the temperature switch 18 is not depressed, the program examines the blood pressure switch 20 to determine whether the user wishes a blood pressure and pulse rate measurement (block 100). If neither the temperature switch 18 nor the blood pressure switch 20 is depressed, the program will return to block 86 and examine the switch 16. However, if the blood pressure switch 20 is depressed, the microprocessor 42 will await input from the pressure sensor 54 and the Korotkoff sound detector 56 in order to determine the user's systolic pressure, diastolic pressure and pulse rate (block 102). The utilization of readings from a pressure sensor and a Kortkoff sound detector to determine these measurements is known in the art and described in U.S. Pat. No. 4,397,317 as well as in the co-pending and commonly owned U.S. Application Ser. No. 653,938. Once the input is received and the calculations performed, the user's systolic pressure, diastolic pressure and pulse rate are displayed in digital form on the liquid crystal display 12 (block 104). The memory switch 24 is then examined in order to determine whether the user wishes to store these measurements (block 106). If the memory switch 24 is depressed the measurements are stored in the non-volatile memory 48 (block 108). Regardless of whether these measurements are stored in the memory, the specific measurements stored in the memory for that day are displayed for 10 seconds before the program returns to block 86 to examine the switch 16 (block 98).

If, at block 86, switch 16 is in the graph position, the program will display a graph showing either the user's systolic pressure, diastolic pressure or pulse rate over a given period of time (75 days) (blocks 110 and 112). The specific measurement to be graphically displayed depends on the position of switch 22. If switch 22 is in the systole position, then a graphic representation of the user's systolic pressure over a given period of time will be displayed; if the switch 22 is in the diastole position, then a graphic representation of the user's diastolic pressure over a given period of time will be displayed; and, if the switch 22 is in the pulse rate position, then a graphic representation of the user's pulse rate over a given period of time will be displayed. It is extremely desirable and important to provide a graphic display of these measurements over a given period of time (approximately two and one half months), as it enables the user and his doctor to detect significant trends in the user's health at early stages. In addition, it permits the user and his doctor to recognize and distinguish minor fluctuations in the measurements. Finally, this capability enables the doctor to conduct long range studies of drug efficacies or other treatments on the user.

Returning to block 110, if switch 16 is in the recorded data position, a digital display showing stored measurements (for the past 75 days) for the user's temperature, blood pressure and pulse rate will be displayed in digital form on the liquid crystal display 12 (block 114). The program will then return to block 86 and examine switch 16.

Figure 4:
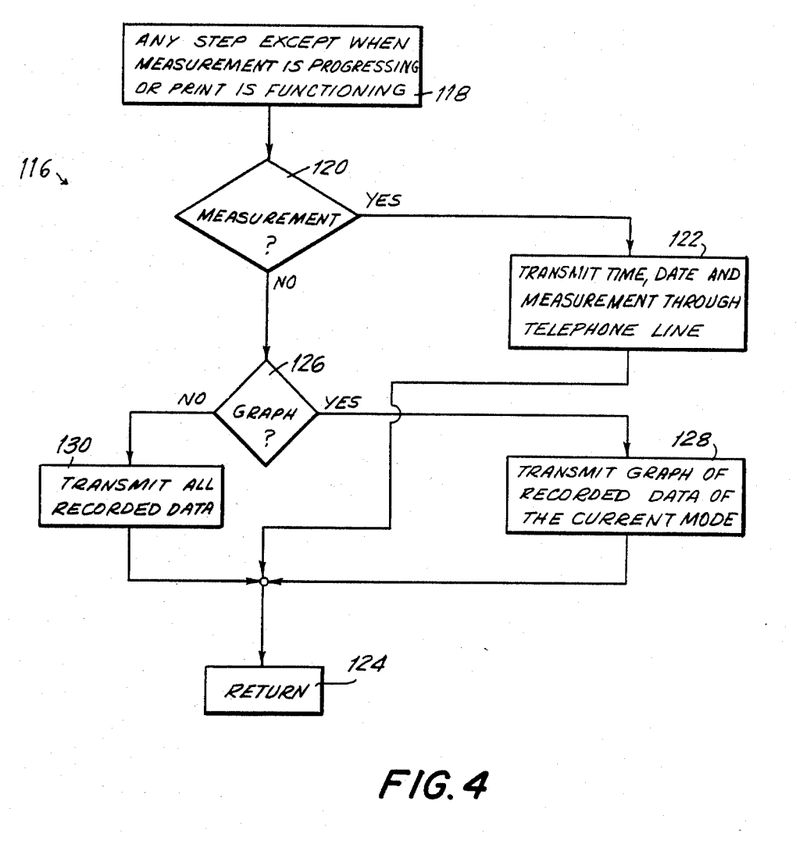
FIG. 4 is a flow chart showing the modem interrupt service subroutine of the electronic circuitry shown in FIG. 2.

Referring now to FIG. 4, a flow chart having the operation of the modem interrupt service subroutine is indicated generally by the reference character 116. The modem interrupt service subroutine 16 is designed to provide the physiological monitor device with the additional ability to transmit data over telephone lines through the use of a modem. This permits the immediate transfer of a specific measurement to a doctor or clinic as well as the transfer of all of the stored measurements and/or graphs showing particular measurements over a given period of time. This capability permits the user to provide his doctor with immediate and practically instantaneous measurements thereby enabling the doctor to provide immediate action if required.

Specifically, upon the actuation of the modem switch 26, the operating routine 80 (FIG. 3) will be interrupted by modem subroutine 116, except with either a measurement is progressing (e.g. blocks 90 and 102 of the operating routine 80) or when the print interrupt service subroutine (shown in FIG. 5) is in operation (block 118). Once the subroutine is initiated, switch 16 is examined and if the switch is in the measurement position, the time, date and the specific measurement just determined is transmitted over a telephone line via a modem 78 (block 122). This permits the user to send an immediate reading of either his temperature or blood pressure to a doctor or clinic, thereby eliminating unnecessary travel by either the doctor or the user. The program then returns to the operating routine 80 at the point of interruption (block 124).

Returning to block 120, if switch 16 is in the graph position the program will form and transmit over a telephone line via a modem, a graph showing either the user's systolic pressure, diastolic pressure or pulse rate over a given period of time. The specific graph transmitted depends upon the position of switch 22 (blocks 126 and 128). The program then exits the modem subroutine 116 and reenters the operating routine 80 at the point of interruption (block 124).

Returning to block 126, if switch 16 is in the recorded data position, the program will transmit (for printing) all of the stored measurements of the user's temperature, systolic and diastolic pressure and pulse rate (block 130); and then return to the main program 80 (block 124).

Figure 5:
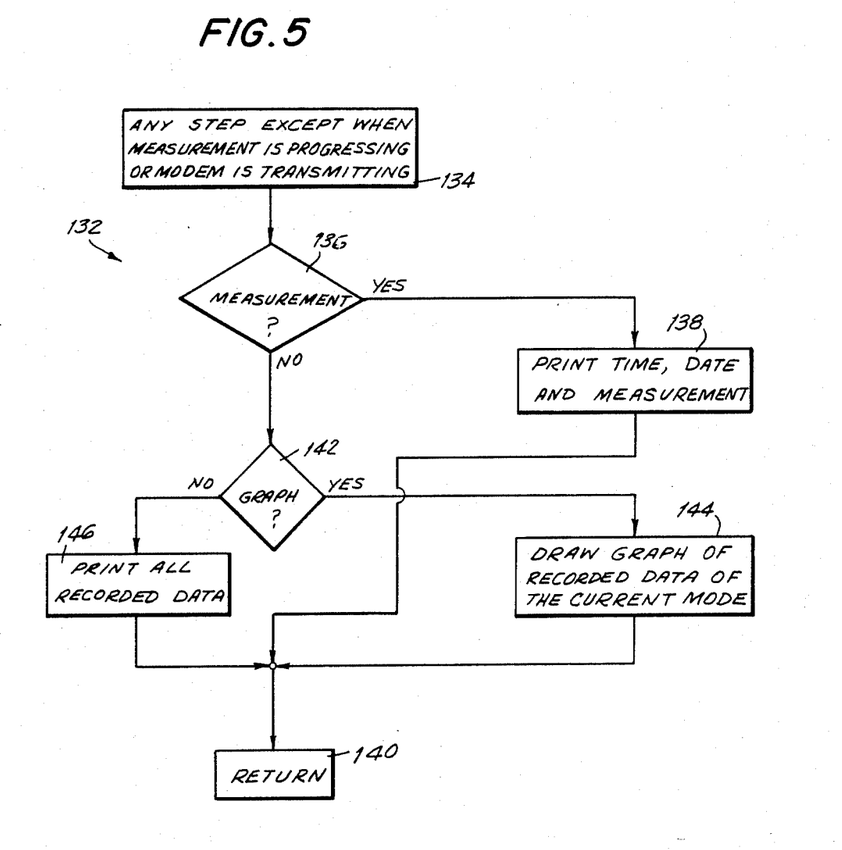
FIG. 5 is a flow chart showing the print interrupt service subroutine of the electronic circuitry shown in FIG. 2.

Referring now to FIG. 5, a flow chart showing the operation of the print interrupt service subroutine is indicated generally by the reference character 132. The purpose of the print subroutine is to enable the user to obtain a hard copy of any or all of the following measurements:

1. The time and date and the specific measurement just completed.
2. A graph of the user's systolic pressure, diastolic pressure or pulse rate over a given period of time.
3. All stored measurements of the user's temperature, blood pressure and pulse rate.

The print interrupt service subroutine may be entered at any time during the operating routine 80, except when a measurement is being taken or the program is in the modem subroutine 116, by depressing the print button 28 (block 134). Once print button 28 is properly actuated, switch 16 is examined (block 136). If the switch is in the measurement position, the printer will be activated to print the date and time and the specific measurement just completed (either temperature or blood pressure and pulse rate) (block 138). With switch 16 in the measurement position and the print button 28 depressed, the device 10 is adapted to give a practically instantaneous hard copy of the specific measurement just completed. As noted above, the printer may be incorporated within the housing 10 or it may be separated therefrom. After the measurement, date and time are printed, the program will exit the print subroutine 132 and reenter the operating routine 80 at the point of interruption (block 140).

Returning to block 136, if switch 16 is in the graph position the printer will be operated to draw a graph showing the stored measurements over a given period of time for either the user's systolic pressure, diastolic pressure or pulse rate, depending upon the position of switch 22 (blocks 142 and 144). The program then exits the printer subroutine 132 and reenters the operating routine 80 at the point of interruption (block 140).

Returning to block 142, if switch 16 is in the recorded data position the printer will print all of the stored measurements of the user's temperature, blood pressure and pulse. For example, if the memory 40 is capable of storing 75 such measurements the printout would look as follows:

| N | TEMP | BP | PULSE |
|---|------|------|-------|
| 0 | 98.0 | 120/70 | 60 |
| 1 | 98.1 | 121/71 | 61 |
| 2 | 98.2 | 122/72 | 62 |
| 3 | 98.3 | 123/73 | 63 |
| 4 | 98.4 | 124/74 | 64 |
| 5 | 98.5 | 125/75 | 65 |
| 6 | 98.5 | 126/76 | 66 |
| . | . | . | . |
| . | . | . | . |
| . | . | . | . |
| 70 | 99.0 | 130/80 | 70 |
| 71 | 99.1 | 131/81 | 71 |
| 72 | 99.2 | 132/82 | 72 |
| 73 | 99.3 | 133/83 | 73 |
| 74 | 99.4 | 143/84 | 74 |
| 75 | 98.0 | 120/70 | 60 |

The program then exits the print subroutine 132 and returns to the operating routine 80 at the point of interruption (block 140).

Figure 6A:
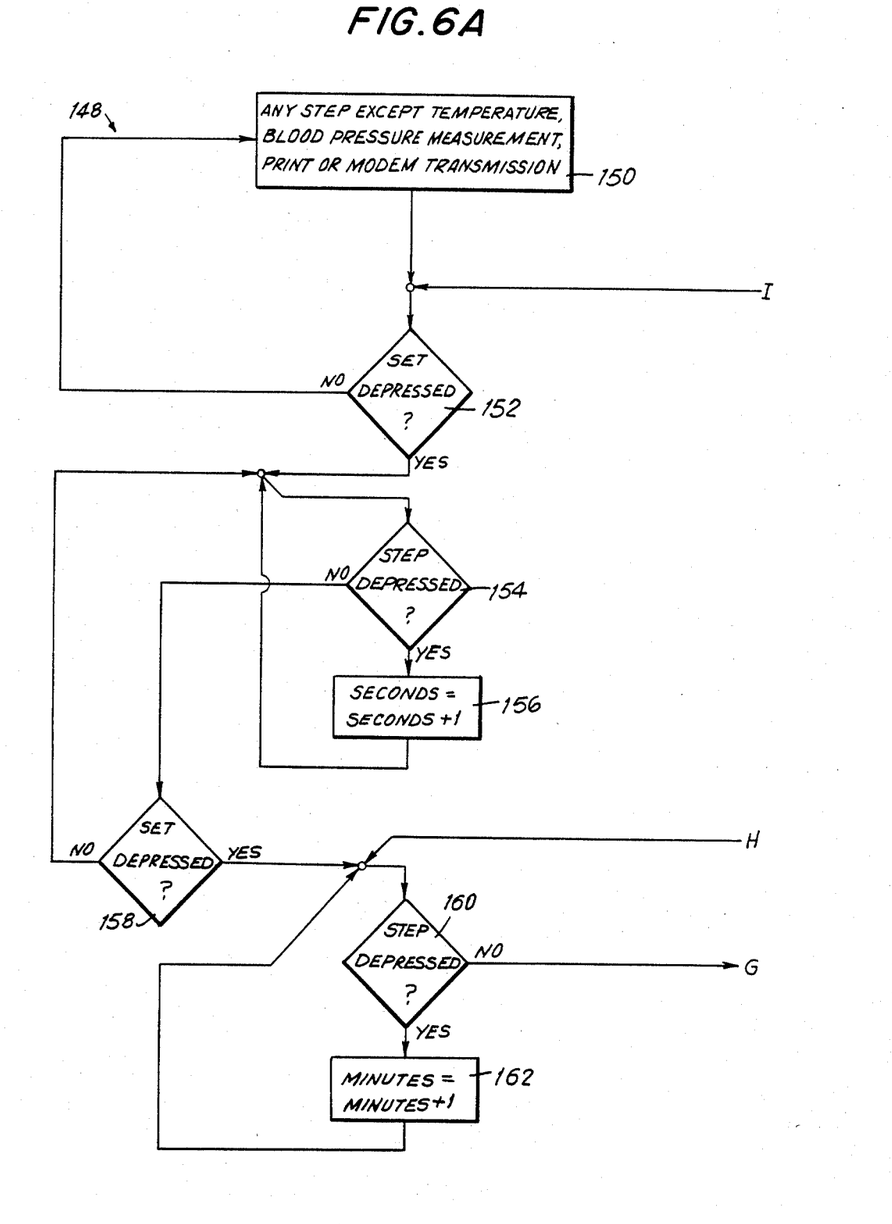
FIGS. 6A and 6B are flow charts showing the time and date adjustment subroutine of the electronic circuitry shown in FIG. 2.
Figure 6B:
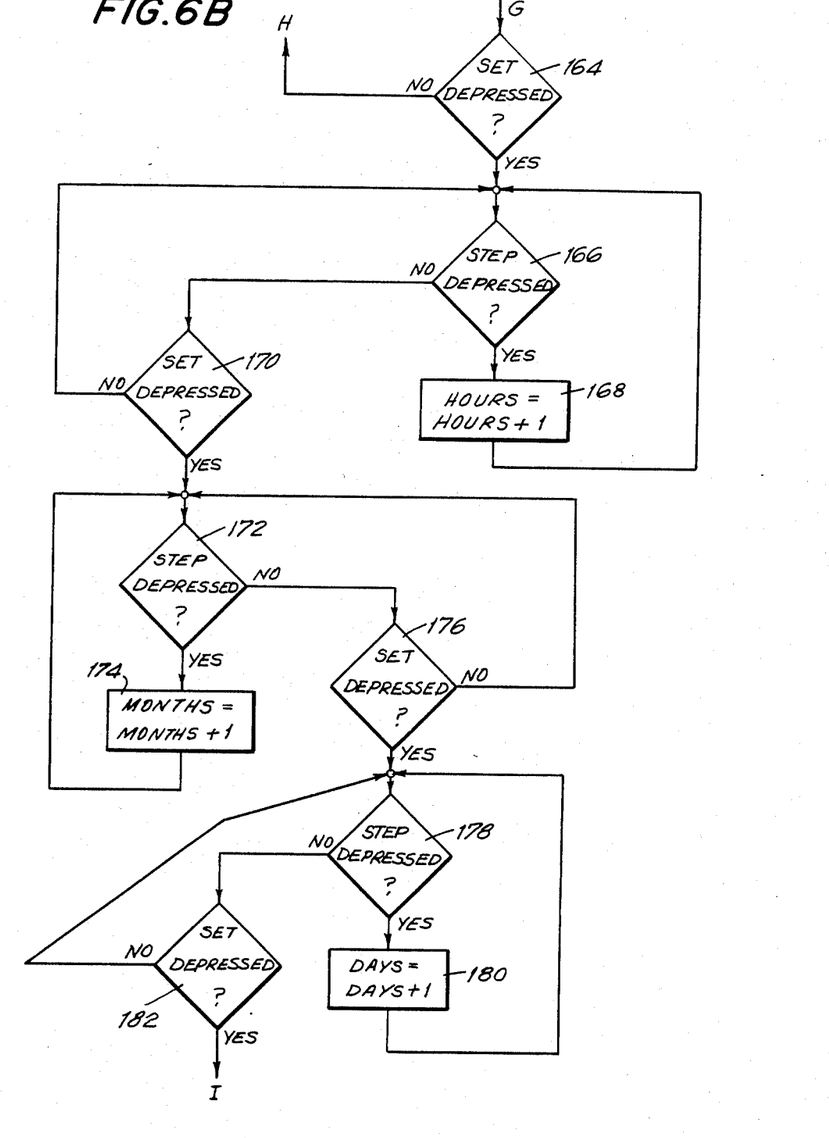

Referring now to FIGS. 6a and 6b a flowchart showing the time and date adjustment subroutine is indicated generally by the reference character 148. The time and date adjustmemt subroutine 148 may be instituted at any time, except during a temperature or blood pressure measurement or when the program is in the modem subroutine 116 or the print subroutine 132 (block 150). The subroutine is initiated by the actuation of the set button 30 (block 152). Upon a depression of the set button 30 the program examines the step button 32 and, if it is depressed, the program slowly increments the seconds display (blocks 152, 154 and 156). The program will continue to increment the seconds display until the step button 32 is released and the set button 30 depressed, which signals that the correct value for the seconds has been entered and appears on the display (block 154 and 158).

The program will then proceed to block 160 and await depression of the step button 32. Upon depression of the step button 32 and for so long as the step button remains depressed, the minutes portion of the display will be slowly incremented (block 162). Once the correct number of minutes appears on the display 12, the step button should be released and the set button 30 depressed (block 164). This indicates that the correct number of minutes has been entered on the display 12.

The program again awaits for the step button 32 to be depressed at which point the hours portion of the display is slowly incremented (blocks 166 and 168). Upon release of the step button 32 and the depression of the set button 30 the incrementing of the hours portion of the display 12 is stopped, indicating that the correct number of hours appears on the display 12 (block 170).

Upon the release of the set button 30 and the depression of the step button 32 the months portion of the display is slowly incremented (blocks 172 and 174). The program will then wait for the release of the step button 32 and the actuation of the set button 30 before terminating the incrementation of the month portion of the display.

After the release of the set button 30 and the depression of the step button 32, the day portion of the display 12 will be slowly incremented (blocks 176, 178 and 180). The number of days will continue to be incremented until the step button 32 is released and the set button 30 depressed (blocks 180, 182). At which point the entire display will have been set and the program will return to block 152.

As will be readily apparent to those skilled in the art, the invention may be used in other specific forms or for other purposes without departing from its spirit or central characteristics. The present embodiments are therefore to be considered as illustrative nd not restrictive, the scope of the invention being indicated by the claims rather than by the foregoing description, and all embodiments which come within the range of equivalence of the claims are intended to be embraced.

We claim:

1. A physiological monitoring device for monitoring a user's physiological condition, comprising sensors adapted to generate first, second and third measurement signals, said first and second measurement signals representative of the user's diastolic and systolic blood pressure and pulse rate, and said third measurement signals representative of the user's body temperature, first, second and third means for converting said respective first, second and third measurement signals into first, second and third processing signals, a microprocessor, a non-volatile memory coupled to said microprocessor, said microprocessor in communication with said first, second and third converting means so as to receive said first, second and third processing signals, first switch means operable to cause said microprocessor to store selected ones of said processing signals in said memory, said memory capable of storing a plurality of said processing signals over a selected period of time, a multiplex in communication with and controlled by said microprocessor, said multiplex adapted to receive output signals from said microprocessor and memory and direct said output signals to any one of a plurality of information output means, said output signals representing information of the user's diastolic and systolic blood pressure, pulse rate and body temperature over a selected time period, said information output means including a screen on which said information is displayed, a printer for printing said information, and means for transmitting said information over a communication link for reproduction at a given location, and second switch means operable to cause said microprocessor to control said multiplex to direct said output signals to one of said information output means, whereby an indication of the user's diastolic and systolic blood pressure, pulse rate and body temperature over a selected period of time is provided.

* * * * *